United States Patent [19]

Ng et al.

[11] Patent Number: 4,788,052
[45] Date of Patent: Nov. 29, 1988

[54] STABLE HYDROGEN PEROXIDE DENTAL GEL CONTAINING FUMED SILICAS

[75] Inventors: Shirley M. Ng, Bridgewater; Denise-Marie DiTomasso, Iselin, both of N.J.

[73] Assignee: Colgate-Palmolive Company, New York, N.Y.

[21] Appl. No.: 40,438

[22] Filed: Apr. 17, 1987

[51] Int. Cl.$^4$ .................... A61K 7/20; A61K 33/40
[52] U.S. Cl. ........................................ 424/53; 424/130
[58] Field of Search ................................ 424/53, 130

[56] References Cited

U.S. PATENT DOCUMENTS

| | | |
|---|---|---|
| 3,639,574 | 2/1972 | Schmolka ............................ 424/130 |
| 4,132,771 | 1/1979 | Schreiber et al. .................... 424/49 |
| 4,159,316 | 6/1979 | Januszewski et al. ................ 424/49 |
| 4,187,287 | 2/1980 | Schreiber et al. .................... 424/49 |
| 4,528,180 | 7/1985 | Schaeffer ............................ 424/130 |
| 4,547,361 | 10/1985 | Stelten Kamp et al. ............. 424/49 |
| 4,562,064 | 12/1985 | Stelten Kamp et al. ............. 424/49 |
| 4,582,701 | 4/1986 | Piechota ............................... 424/49 |
| 4,647,451 | 3/1987 | Piechota ............................... 424/49 |
| 4,696,757 | 9/1987 | Blank et al. .......................... 424/53 |

*Primary Examiner*—Shep K. Rose
*Attorney, Agent, or Firm*—Robert L. Stone; Murray M. Grill

[57] ABSTRACT

A stable aqueous hydrogen peroxide gel dentifrice for oral anti-gingivitis application having an acid pH of about 3–6 comprising a combination of hydrophilic and hydrophobic fumed silica gelling agent, hydrogen peroxide, about 20–40% by weight of a polyethylene glycol humectant, flavor, sweetening agent, sodium benzoate, and a nonionic surfactant as the essential ingredients, prepared by a process which comprises controlling the order of addition of the essential ingredients. Distilled (deionized) water is preferred in the formulation to prevent minimal contamination.

7 Claims, No Drawings

STABLE HYDROGEN PEROXIDE DENTAL GEL CONTAINING FUMED SILICAS

BACKGROUND AND PRIOR ART

The present invention relates to the formation of a cosmetic and chemically stable hydrogen peroxide-containing dental gel having an acid pH of about 3–6 comprising a compatible system of specified amounts of specific dental components, desirably prepared by a specific order of addition of the various ingredients.

Until now it has been difficult to formulate a cosmetic and chemically stable hydrogen peroxide gel with appropriate thickening/gelling agents, humectant, surfactants and flavor for oral application. However, after extensive experimentation on various mixtures of components in the hydrogen-peroxide dental gel product, a compatible system of water, a combination of hydrophilic and hydrophobic fumed silica as gelling agent, polyethylene glycol humectant, nonionic surfactant, sweetening agent, sodium benzoate, and flavor has been discovered. It has also been found that the order of addition of these ingredients is important in the formation of a stable gel.

Accordingly, it has been discovered that by using a specific sequential step process, stable formulations of a hydrogen peroxide dental gel containing a combination of hydrophilic and hydrophobic fumed silica as gelling agent, a polyethylene glycol hymectant, a nonionic surfactant, sweetening agent, sodium benzoate, and flavor can be made. The stable hydrogen peroxide gel is prepared by homogenizing the fumed silicas in the polyethylene glycol and water phases and the sequential addition of the premixed homogenized hydrophobic fumed silica in the polyethylene glycol (Phase A) to the premixed homogenized hydrophilic fumed silica in water containing hydrogen peroxide (Phase B) and mixing for about 30 minutes while maintaining the temperature at room temperature, adding the predissolved sodium saccharin and sodium benzoate in water (Phase C) with mixing which effects immediate gellation, adding the presolubilized flavor in the nonionic surfactant and water (Phase D) and mixing for about 5–10 minutes until a clear, homogeneous rigid stable dental gel is obtained.

The finished oral product is a stable rigid gel having improved chemical and cosmetic stability and improved taste.

It has long been recognized in the art that hydrogen peroxide and other peroxygen-containing agents are effective in curative and/or prophylactic treatments with respect to caries, dental plaque, gingivitis, periodontitis, mouth odor, tooth stains, recurrent aphthous ulcers, denture irritations, orthodontic appliance lesion, post extraction and postperiodontal surgery, traumatic oral lesions and mucosal infections, herpetic stomatitis and the like. Peroxide-containing agents in the oral cavity exert a chemomethanical action generating thousands of tiny oxygen bubbles produced by interaction with tissue and salivary enzymes.

Peroxide mouthrinses and other oral preparations prevent colonization and multiplication of anaerobic bacteria known to be associated with periodontal disease. Peroxygen-containing gels or pastes are indicated and/or desirable where it is required to selectively treat areas for more than a few seconds, such gels and pastes tending to remain at the site of application for a time sufficient for the peroxide to manifest its maximum effectiveness.

It is also known that most peroxy compounds such as hydrogen peroxide in oral compositions tend to be unstable in storage due to incompatibility with and/or interaction with other common ingredients in the composition, and lose the capacity to release active or nascent oxygen over relatively short periods of time. This adversely affects both the chemical stability of the composition as well as the cosmetic stability of the final product, particularly in the gel product containing hydrogen peroxide.

The prior art has attempted to solve said problems by using a variety of stabilizers for dental compositions in assorted forms such as tablets, chewing gum, mouthwashes, toothpastes, or powder containing a hydrogen peroxide as shown in U.S. Pat. No. 4,226,851 wherein is disclosed an aqueous mouthwash containing hydrogen peroxide, flavor, zinc chloride and water soluble Vitamin E which stabilizes the hydrogen peroxide in the mouthwash. U.S. Pat. No. 4,302,441 discloses solid oral products (tablets and chewing gum) containing urea hydrogen peroxide in gum bases such as jelutong, rubber latex, vinylate resins, etc., and in methyl, ethyl and sodium carboxymethyl cellulose carriers, free of glycerol, also containing sweeteners such as sodium saccharinate, xylitol, sorbitol, and mannitol and flavors. U.S. Pat. No. 4,476,108 discloses an admixture of peroxidase, a peroxide and a donor molecule such as phenylethylamine, tyrosine, tryptophan, benzoic acid, salicylic acid, hydroquinone, dehydrophenyl-alanine, vanillan and para-aminobenzoic acid, in a carrier such as water (mouthwash) or in the form of a paste, gel or powder. U.S. Pat. No. 4,431,631 discloses an aqueous oral solution containing hydrogen peroxide, glycerin and/or sorbitol humectant, 0.5–3% pluronic-type surfactant, polyoxyethylenated sorbitol monofatty acid esters surfactant, sweetener and flavor.

The prior art also discloses dental compositions containing a hydrogen peroxide and an additional component to effect stabilization, such as ascorbic acid in U.S. Pat. No. 3,886,265, wherein is discloses tablets, lozenges, chewing gum or an aerosol or spray from containing a peroxide such as hydrogen peroxide and an ene-diol compound such as ascorbic acid, effective against bad breath.

U.S. Pat. No. 4,521,403 discloses a method of controlling and treating periodontal diseases by washing the teeth with an aqueous or aqueous alcoholic solution of a hydrogen peroxide and a povidone-iodine complex (complex of iodine with 1-vinyl-2-pyrrolidone polymers). These two ingredients are mixed only prior to use. U.S. Pat. No. 4,592,487 discloses an antiplaque dentifrice in the form of a toothpaste or gel containing the two components, a peroxide and povidone-iodone complex, each separately mixed with conventional dentrifice components, and kept separated until admixed and dispensed from a special dual compartment container/mixer/dispenser device. U.S. Pat. No. 4,592,488 discloses an oral mouthwash containing an iodophor or quaternary ammonium compound and a peroxide compound such as hydrogen peroxide in the form of an aqueous or aqueous alcoholic solution prior to combining the two components into an oral mouthwash. U.S. Pat. No. 4,592,489 discloses a two-part container for dispensing an oral mouthwash containing the povidone-iodine complex solution separate from the hydrogen peroxide solution and mixing prior to dispensing.

Dental compositions containing other oxidizing agents in lieu of the hydrogen peroxide are also disclosed in the prior art. U.S. Pat. No. 4,405,599 discloses toothpaste containing an oxidizing agent such as carbamide peroxide (urea peroxide) which dissociates into urea and hydrogen peroxide in the oral cavity, in a paste carrier comprising an anionic detergent, sorbitol and glycerin humectant and a thickening agent such as gum tragacanth, sodium alginate or sodium carboxymethyl cellulose.

U.S. Pat. No. 4,405,599 discloses toothpaste containing calcium peroxide and sodium perborate oxidizing agents; dicalcium phosphate, calcium carbonate and magnesium carbonate cleaning agents; sorbitol humectant; cornstarch and cellulose gum thickening agents, and an anionic detergent.

However, none of the aforesaid patent disclose the preparation of hydrogen peroxide gels containing the essential specific components of a polyethylene glycol humectant, a nonionic surfactant, flavor, sodium saccharin, sodium benzoate and a combination of hydrophilic and hydrophobic fumed silica gelling/thickening agent in the formation of a stable dental gel.

The prior art also discloses processes of preparing peroxide gel as shown in U.S. Pat. No. 3,657,413 and the article by Assasy et al, "Stability of Hydrogen Peroxide in Certain Pharmaceutical Gels" Cosmetics and Toiletries 54–56, 91, September 1976. The patent discloses a clear gel comprising urea peroxide, glycerol, a carboxypolymethylene polymer and flavor; prepared by dispersing the polymer into the glycerol with high speed stirring at reduced pressure and then dissolving the urea peroxide and other ingredients in the thickened polymer/glycerol solution yielding a viscous gel. The article discloses methyl cellulose gels for treating surface cuts, bleaching hair and for deodorant purposes containing 0.1% oxine as stabilizer for the hydrogen peroxide; prepared by dispersing the methyl cellulose in water using an electric stirrer and then neutralizing the triethanolamine to yield a gel; or dispersing in hot water until well hydrated, refrigerating until solidified and stirring until a gel is obtained, adding the stabilizing oxine to the gel, followed by the addition of the hydrogen peroxide. Other stabilizers which are not as effect as oxine include hexamine, benzoic acid or urea.

Hydrogen peroxide gels containing polyoxyethylene polyoxypropylene block copolymers as the gelling/thickening agent is disclosed in U.S. Pat. No. 3,639,574 which discloses a stable hydrogen peroxide gel for use in hair bleaching and treating surface cuts, using polyoxyethylene polyoxypropylene block copolymers as gelling agents in amounts of 22–79% of the total compositions, which may be prepared by dissolving the copolymers in water cooled to a temperature of 35°–50° F. and slowly adding the hydrogen peroxide to the cool polymer solution, allowing the solution to warm up to room temperature which forms a clear gel. This method may be varied by first adding the $H_2O_2$ to cold water and then adding the copolymer to the cold aqueous solution and mixing until completely dissolved, followed by standing at room temperature until it gels. This is not a dental gel, does not contain the polyethylene glycol humectant, sodium saccharine sweetener, or flavor which are essential ingredients in the dental gel.

Denture cleansers containing 0.5–1.0% CAB-O-Sil, a colloidal, submicroscopic, pyrogenic silica, to maintain a mixture of solid ingredients in a free-flowing state and to prevent lumping is disclosed in U.S. Pat. No. 3,372,125.

U.S. Pat. No. 4,223,003 discloses toothpaste and powder dentifrices containing a dye, a high foaming surfactant (anionic) to produce colored foam when brushing the teeth, a peroxide-containing compound such as magnesium peroxide, and conventional dental constituents which include carboxymethyl cellulose thickeners, pyrogenic silica, humectants, polishing agents, flavors, fluorides, etc.

U.S. Pat. No. 4,537,765 discloses a toothpaste having a pH of 9.2–10.5 containing a peroxydiphosphate salt, a polyethylene glycol humectant, a thickener such as colloidal silica, carboxyvinyl polymer, cellulose gums, or hectorite, a polishing agent such as silica or hydrated alumina and anionic or nonionic surfactants such as Pluronic F108.

However, the prior art does not disclose a cosmetic and chemically stable aqueous hydrogen peroxide dental gel having a pH of 3–6 containing as the essential ingredients a combination of hydrophilic and hydrophobic fumed silica gelling agent, a polyethylene glycol humectant, a nonionic surfactant, sweetening agent, sodium benzoate, and flavor prepared by a novel process utilizing a specific sequence of steps, which comprises the sequential addition with mixing of Phase A, a premixed homogenized hydrophobic fumed silica in polyethylene glycol; to Phase B, of premixed homogenized hydrophilic fumed silica in water containing hydrogen peroxide, and mixing for about 30 minutes at room temperature; adding Phase C, predissolved sodium saccharin and sodium benzoate in water to Phase AB to effect gelation; adding Phase D, pre-solubilized flavor in the nonionic surfactant and water to Phase ABC and mixing for about 5–10 minutes until a clear, and homogeneous rigid gel is obtained.

SUMMARY OF THE INVENTION

It has now been found that an aqueous hydrogen peroxide dental gel can be stabilized in the presence of polyethylene glycol, sodium saccharin, sodium benzoate, nonionic surfactant and flavor when using a combination of hydrophilic and hydrophobic fumed silica at a level of about 8–10% by weight hydrophilic fumed silica and 0.5–1.5% by weight hydrophobic fumed silica as the gelling agent. The fumed silica gelling agents are compatible with the aqueous hydrogen peroxide, whereas the natural gums derived from organic material such as alginates, methyl cellulose and the like, are degraded by the hydrogen peroxide resulting in unstable gels. Similarly, synthetic organic polymers such a polyvinyl pyrrolidone form a stringy gel, which is not the clear homogeneous rigid gel in accordance with the present novel dental gel product. The presence of stabilizers such as sodium stannate, sodium pyrophosphate, oxine EDTA and calcium disodium EDTA have been found to be unnecessary and undesirable because their presence provide no advantages to the composition. Their presence tend to adversely affect the chemical stability of the $H_2O_2$. The combination of polyethylene glycol humectant and the fumed silicas gelling agent has been found to yield a more stable rigid gel than a gel prepared in the absence of the polyethylene glycol. The presence of nonionic surfactants have been found to have acceptable stability in an aqueous peroxide environment. The anionic surfactants do not have acceptable stability in the presence of hydrogen peroxide. Accordingly, the formulation of present novel stable hydrogen peroxide dental gel is based on the specificity of compatible ingredients.

It has additionally been found that a novel process of preparing the hydrogen peroxide gel further assists in the obtention of a stable $H_2O_2$ gel. The process utilizes a specific sequence of steps which comprises the formation of four separate phases:

Phase A comprising hydrophobic fumed silica dispersed in polyethylene glycol by mixing until homogeneous, Phase B comprising hydrophilic fumed silica and hydrogen peroxide dissolved in water, Phase C comprising sodium saccharin and sodium benzoate dissolved in water, and Phase D comprising flavor solubilized in nonionic surfactant and water; and sequentially adding Phase A to Phase B and mixing until a homogeneous translucent liquid is obtained, and further homogenizing this mixture at room temperature for about thirty minutes; admixing Phase C with Phases AB which forms a gel; adding Phase D to Phase ABC and mixing for about 5-10 minutes to form a rigid clear homogeneous stable dental gel. The stable gel product may be acidified to a pH of about 3-6 with an appropriate acid such as citric acid or phosphoric acid, if needed. The final product may be packaged in any suitble container compatible with the hydrogen peroxide, such as plastic or metal tubes; or in a dual compartment container or kit with a bicarbonate dentifrice.

Accordingly, a primary object of the present invention is to formulate a cosmetically and chemically stable hydrogen peroxide oral gel having a pH of about 3-6 and preferably 4.5-5 containing a combination of hydrophilic and hydrophobic fumed silica as gelling agent in amounts of about 8-10% by weight hydrophilic fumed silica and about 0.5-1.5% by weight hydrophobic fumed silica which is compatible with the $H_2O_2$.

Another object of this invention is to provide a cosmetically stable $H_2O_2$-combined hydrophilic and hydrophobic fumed silica gel containing polyethylene glycol humectant which is compatible with the other dental ingredients.

Still another object of this invention is to provide a cosmetically and chemically stable aqueous $H_2O_2$ dental gel having improved taste containing a compatible formulation of the fumed silica gelling agent, polyethylene glycol humectant, nonionic surfactant, flavor, sweetening agent such as sodium saccharin and sodium benzoate.

Another object of this invention is to formulate a stable $H_2O_2$ dental gel based on the hydrophilic and hydrophobic fumed silica gelling agent, with improved compatability of all components by using a novel process comprising a specific order of addition of the various ingredients.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combination particularly pointed out in the appended claims.

To achieve the foregoing and other objects and in accordance with the present invention, as embodied and broadly described herein, the novel stable aqueous hydrogen peroxide dental gel of this invention comprises about 1.5-3.5% by weight $H_2O_2$ as the sole chemically active agent, about 8-10% by weight hydrophilic fumed silica and 0.5-1.5% by weight hydrophobic fumed silica as gelling agent, about 20-40% by weight polyethylene glycol humectant, a nonionic surfactant, sweetener, flavor and sodium benzoate, said gel having an acid pH of about 3-6. Sodium saccharin is the preferred sweetener. Sodium benzoate is an essential additive in the gellation of the formulation. The water content in the gel constitutes about 20-40% by weight of the dental composition. Distilled or deionized water is preferred to prevent minimal contamination.

The stable hydrogen peroxide dental gel of this invention is prepared by a novel process comprising separately homogenizing the hydrophobic fumed silica in the polyethylene glycol forming Phase A; and the hydrophilic fumed silica in the formula amount of water containing the hydrogen peroxide, Phase B; and mixing the two phases to form a translucent liquid; sequentially admixing Phase C consisting of sodium saccharin and sodium benzoate dissolved in water, with the transulcent liquid of Phase AB to form a gel; and admixing Phase D consisting of flavors solubilized in the nonionic surfactant and water, with the gel of Phase ABC to obtain a clear, homogeneous, rigid, stable dental gel.

This order of addition of the specific ingredients is essential to the formation of a stable hydrogen peroxide dental gel. No gellation occurs if sodium benzoate is eliminated from the formulation. Likewise, if Phase D is added to Phase AB prior to Phace C, no gellation is observed.

More specifically, present invention relates to a novel process of preparing a cosmetic and chemically stable aqueous $H_2O_2$ dental gel comprising a combination of hydrophilic and hydrophobic fumed silica gelling/thickening agent, a polyethylene glycol humectant, a nonionic surfactant, a sweetener, sodium benzoate, and a flavor, consisting essentially of homogenizing the fumed silicas in the polyethylene glycol and water phases by the sequential addition of the premixed homogenized hydrophobic fumed silica in the polyethylene glycol (Phase A) to the premixed homogenized hydrophilic fumed silica in water containing hydrogen peroxide (Phase B) and mixing for about 30 minutes while maintaining the temperature at room temperature, adding the predissolved sodium saccharin and sodium benzoate in water (Phase C) with mixing which effects immediate gellation, adding the presolubilized flavor in the nonionic surfactant and water (Phase D) and mixing for about 5-10 minutes until a clear, homogeneous rigid stable dental gel is obtained.

The hydrogen peroxide formulation of present invention contains an effective amount of hydrogen peroxide for oral antigingivitis application, preferably about 1.5-3.5% by weight of the composition. Hydrogen peroxide is usually supplied as 30-35% aqueous solutions containing 1.5-3.5% active ingredient. The hydrogen peroxide is stable in the presence of polyethylene glycol, sodium saccharin, nonionic surfactant, favor, and the fumed silica gelling agent.

An essential ingredient in present $H_2O_2$ gel dentifrice is a compatible peroxide-stable thickening and gelling agent which is a combination of hydrophilic and hydrophobic fumed siclia in amounts of about 8-10% by weight hydrophilic fumed silica and about 0.5-1.5% by weight of hydrophobic fumed silica. The preferred weight ratio of the fumed silica mixture in present dentifrice gel is within the range of 16:1 to 6:1 hydrophilic to hydrophobic fumed silica. The combination of hydrophilic and hydrophobic fumed silica provides greater stability properties to the hydrogen peroxide gel than with the use of a single fumed silica or other type of colloidal silica. This combination passes the freeze/thaw cycle without showing separation. Three weeks of aging of several formulations showed significant improvement in the cosmetic stability of the hydrogen peroxide gel. Fumed silica is a coagulated silicon dioxide of extremely small particle size, produced by the hydrolysis of silicon tetrachloride vapor in a flame of hydrogen and oxygen; and is described in *Cosmetic Technology,* March 1980 pp 35–39, by John Hardy and William F. Moll Jr. in an article entitled "The Use of Fumed Silica in Cosmetics". In this combustion process, molten spheres of silica are formed having average diameter of 7 to 14 millimicrons and final surface areas ranging from 400 square meters per gram ($m^2/g$) to 200 $m^2/g$. The molten spheres fuse with one another to form branched three-dimensional, chain-like aggregates. During the formation of fumed silica, three types of hydroxyl groups are produced, isolated hydroxyls, hydrogen-bonded hydroxyls and siloxane (Si—O—Si). The isolated and the hydrogen-bonded hydroxyl groups are sites of hydrophilicity, whereas the siloxane is non-polar and hydrophobic. Fumed silica is a dry powder obtainable as "Aerosil" from degussa. Various types of Aerosils are available depending on the variations in the manufacturing process. Aerosil 200 is a hydrophilic fumed silica, having a surface area of 200±25 square meters per gram, an average particle size of about 10-12 nanometers and a compacted apparent density of about 50 g/l. Aerosil with surface areas greater than 200 $m^2/g$ such as Aerosil 300 and Aerosil 380 may also be used. Aerosil R972 is a hydrophobic fumed silica having a surface area of 110±20 $m^2/g$ and an average particle size of 16 nanometers and a compacted apparent density of about 50 g/l.

Another essential ingredient in the $H_2O_2$ gel formulation of present invention is the polyethylene glycol humectant which is compatible with the hydrogen peroxide, the nonionic surfactant, flavor and the fumed silica gelling agent.

Polyethylene glycols known by the trademark CARBOWAX are nonionic polymers of ethylene oxide having the general formula:

wherein n represents the average number of oxyethylene groups. The Carbowax polyethylene glycols are designated by a number such as 400, 600, etc. which represents the approximate average molecular weight. The polyethylene glycols 200, 300, 400 and 600 are clear viscous liquids at room temperature. They are less hygroscopic than glycerin and simple glycols, are water soluble and form a clear aqueous solution. The polyethylene glycols provide a different and better feel and taste to the dental product than the glycerin or sorbitol. It has been found that the polyethylene glycol humectant aids in making a superior stable rigid $H_2O_2$ gel compared to the gel with glycerin. The polyethylene glycol humectant constitutes about 20–40% by weight of the $H_2O_2$ gel compared to the gel with glycerin. The polyethylene glycol humectant constitutes about 20–40% by weight of the $H_2O_2$ gel formulation. Typically, the average molecular weight of polyethylene glycol humectant is up to about 1000, preferably about 400–600 and most preferably about 600.

Another essential ingredient in the aqueous $H_2O_2$ gel formulation of this invention is the nonionic surfactant which is compatible with the $H_2O_2$ and is peroxide-stable. The nonionic surfactant serves as a solubilizing, dispersing, emulsifying and wetting agent and is especially effective to solubilize the flavor. A particularly useful nonionic surfactant is a water soluble polyoxyethylene monoester of sorbitol with a $C_{10}$ to $C_{18}$ fatty acid, known under the Tween Trademark. The Tween surfactants are mixtures of $C_{10}$-$C_{18}$ fatty acid esters of sorbitol (and sorbitol anhydrides), consisting predominatnly of the monoester, condensed with about 10–30, preferably about 20, moles of ethyleneoxide. The fatty acid (aliphatic hydrocarbonyl monocarboxylic acid) may be saturated or unsaturated, e.g. lauric, palmitic, stearic, oleic acids. Polysorbate 20 (e.g. Tween 20) is especially preferred and is commonly referred to as polyoxyethylene (20) sorbitan monolaurate. The nonionic surfactant constitutes about 0.5–5.0% by weight and preferably 0.5–3% by weight of the gel composition.

Another essential ingredient of present aqueous $H_2O_2$ gel dentifrice is an effective flavoring amount of a flavor compatible with and stable in the presence of hydrogen peroxide. The flavor ingredient constitutes about 0.5–2% by weight of the composition. Suitable flavoring constituents are flavoring oils, e.g. oils of spearmint, peppermint, wintergreen, sassafras, clove, sage, eucalyptus, majoram, cinnamon and methyl salicylate and menthol.

A sweetening material is also employed as a complement to the flavoring material. Suitable sweetening agents are water soluble and include sodium saccharin, sodium cyclamate, xylitol, perillartine, D-tryptophan, aspartame, dihydrochalcones and the like, in concentrations of about 0.01 to 1.0% by weight. Sodium saccharin is preferred.

The pH of the $H_2O_2$ gel dentifrice of the invention ranges from 3–6, preferably about 4.5 to 5 for optimum use in the oral cavity. A pH less than 4.5 may be too acid for optimum use in the oral cavity and at a pH greater than 5 the stability of the gel is diminished. The pH of the prepared composition is generally adjusted to 5.0 with an appropriate acid such as phosphoric acid or citric acid. The acidic pH affords greater stability to the gel product of present invention. The lower the pH, the greater the stability.

The hydrogen peroxide gel dentifrice of this invention may also contain conventional additional ingredients such as coloring or whitening agents, or preservatives in minimal amounts of up to 5% by weight and preferably up to 1%, provided they do not interfere with the chemical and cosmetic (physical) stability properties of the finished product.

It has been found that by specifically utilizing the specific combination of ingredients of nonionic surfactant, polyethylene glycol humectant, the combination of hydrophilic and hydrophobic fumed silica gelling agent, sweetening agent, sodium benzoate and flavor, a cosmetic and chemically stable aqueous hydrogen peroxide gel dentifrice having improved taste can be formulated.

It has additionally been found that the new formulation method of homogenizing the fumed silicas in the polyethylene glycol and water phases and the sequential addition of Phase A, B, C and D, using the specific ingredients of gelling agent, humectant, nonionic surfactant, sodium benzoate, sweetening agent (sodium saccharin) and flavor provides superior chemical and cosmetic stability to an aqueous hydrogen peroxide gel dentifrice having improved taste.

The final product is a rigid ringing gel which may be described as gels that have a firm jelly-like consistency; that is, when said gel is packaged in a jar type container and the sides of said container are tapped lightly, the gel vibrates but retains its original configuration. The dental gel product of present invention is a dentifrice and not a mouthrinse, and will dissolve in the oral cavity only upon brushing.

In the practice of this invention to promote oral hygiene, the gel dentifrice according to this invention is applied regularly to dental enamel by brushing the teeth for 30–90 seconds at least once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated.

EXAMPLES 1 AND 2

| Phases | Ingredients | Percentage EX 1 | Ex 2 |
|---|---|---|---|
| A | Polyethylene glycol 600 (Union Carbide) | 40.0 | 40.0 |
|   | Aerosil R972 (Degussa) | 0.5 | 1.5 |
| B | Distilled, deionized water | 33.65 | 11.00 |
|   | Aerosil 200 (Degussa) | 8.0 | 9.0 |
|   | $H_2O_2$ (35% Aqueous Solu) | 8.6 | 28.6 |
| C | Distilled, deionized water | 1.5 | 1.5 |
|   | Sodium Saccharin | 0.2 | 0.2 |
|   | Sodium Benzoate | 0.35 | 0.5 |
| D | Distilled, deionized water | 5.0 | 5.0 |
|   | Polyoxyethylene (20) Sorbitan monolaurate | 1.2 | 1.2 |
|   | Flavor | 1.0 | 1.5 |
|   | pH: app. 4.5–5 | | |

Procedure:
Steps:

1. Aerosil R972 (hydrophobic fumed silica) is dispersed in PEG-600 with a lightnin mixer until homogenous.
2. Phase A is added to Phase B and pre-mixed in the Hobart mixer or Ross mixer until homogeneous (translucent liquid).
3. The above mixture is further homogenized with a Homomixer for an additional 30 minutes while the temperature was maintained at room temperature.
4. The pre-dissolved sodium saccharin and sodium benzoate (Phase C) are added to Phase AB while homomixing. Gellation is immediate.
5. Phase ABC is transferred to a Ross or Hobart mixer. The pre-solubilized flavor (Phase D) is then added, and mixed for an additional 5–10 minutes. A stable gel is formed.

EXAMPLE 3

Example 1 is repeated except that polyethylene glycol 400 is substituted for the polyethylene glycol 600. The end product is equally effective against gingivitis related bacteria, and also exhibits excellent chemical and cosmetic stability properties.

EXAMPLES 4 AND 5

| Ingredients | % Example 4 | Example 5 |
|---|---|---|
| Polyethylene glycol 600 (Union Carbide) | 20.0 | 40.0 |
| Aerosil 200 (Degussa) | 8.0 | 10.0 |
| Aerosil R972 (Degussa) | 0.5 | 1.0 |
| Hydrogen peroxide (35% aqueous solu) | 8.6 | 8.6 |
| Sodium Saccharin | 0.2 | 0.2 |
| Sodium Benzoate | 0.35 | 0.5 |
| Polyoxyethy (20) Sorbitan Monolaurate | 1.0 | 1.2 |
| Flavor | 1.0 | 1.5 |
| Distilled, deionized water | 60.35 | 37.0 |
| pH: app. 4.5–5.0 | | |

The above dental hydrogen peroxide gel formulations are prepared by the same procedure outlined in Example 1. The final dentifrice products of Examples 4 and 5 also exhibit excellent storage stability and are in the form of a stable rigid clear gel.

This invention has been disclosed with respect to preferred embodiments, and various modifications and variations thereof obvious to those skilled in the art are to be included within the spirit and purview of this application and the scope of the appended claims.

What is claimed is:

1. A cosmetic and chemically stable aqueous hydrogen peroxide dental gel having a pH between about 3–6, comprising hydrogen peroxide as the sole chemically active agent in an amount of 1.5–3.5% by weight, a combination of hydrophilic and hydrophobic fumed silica gelling agent, about 20–40% by weight of a polyethylene glycol humectant, a nonionic surfactant, a sweetener, sodium benzoate and a flavor prepared by homogenizing the fumed silicas in the polyethylene glycol and water phases and the sequential addition of the premixed homogenized hydrophobic fumed silica in the polyethylene glycol (Phase A) to the premixed homogenized hydrophilic fumed silica in water containing hydrogen peroxide (Phase B) and mixing for about 30 minutes while maintaining the temperature at room temperature, adding the predissolved sodium saccharin and sodium benzoate in water (Phase C) with mixing which effects immediate gellation, adding the presolubilized flavor in the nonionic surfactant and water (Phase D) and mixing for about 5–10 minutes until a clear, homogeneous rigid stable dental gel is obtained.

2. The dental gel according to claim 1, wherein the pH is adjusted to about 4.5–5 with an acid.

3. The dental gel according to claim 1, wherein the hydrophilic fumed silica constitutes about 8 to 10% by weight and the hydrophilic fumed silica constitutes about 0.1 to 1.5% by weight of the composition.

4. The dental gel according to claim 1, wherein the polyethylene glycol humectant has a molecular weight of 600.

5. The dental gel according to claim 1 wherein the nonionic surfactant is a polyoxyethylene monoester or sorbitol with a $C_{10}$ to $C_{18}$ fatty acid in an amount of about 0.5–3% by weight.

6. The dental gel according to claim 1, wherein the sodium benzoate constitutes 0.35 to 0.5% by weight.

7. The dental gel according to claim 1, wherein the sweetening agent is sodium saccharine and the nonionic surfactant is polyethylene (20) sorbitan monolaurate.

* * * * *